US006833141B1

(12) United States Patent
Owades

(10) Patent No.: US 6,833,141 B1
(45) Date of Patent: Dec. 21, 2004

(54) METHOD OF TREATING PRURITIS AND COMPOSITION THEREOF

(76) Inventor: Joseph L. Owades, 3097 Wood Valley Rd., Sonoma, CA (US) 95476

( * ) Notice: Subject to any disclaimer, the term of this patent is extended or adjusted under 35 U.S.C. 154(b) by 0 days.

(21) Appl. No.: 10/617,501

(22) Filed: Jul. 11, 2003

(51) Int. Cl.$^7$ ............................................... A61K 33/04
(52) U.S. Cl. ...................................................... 424/703
(58) Field of Search .......................................... 424/703

(56) References Cited

U.S. PATENT DOCUMENTS 2,884,352 A    4/1959  Brenner et al. ............... 167/20
4,880,627 A  * 11/1989  Trenzeluk .................... 424/640

FOREIGN PATENT DOCUMENTS

DE           3514724     * 10/1986

* cited by examiner

Primary Examiner—Alton Pryor
(74) Attorney, Agent, or Firm—Hayes Soloway P.C.

(57) ABSTRACT

A composition and method of treating severe itching by topically administering a therapeutically effective amount of colloidal sulfur suspended in a pharmaceutically acceptable carrier including a diketone.

14 Claims, No Drawings

METHOD OF TREATING PRURITIS AND COMPOSITION THEREOF

BACKGROUND OF THE INVENTION

Itching or Pruritis is a common dermatoloigical symptom. The causes of Pruritis are complex and not completely understood. Among the causes of itching are localized causes such as eczema of the scalp and fingers, general Pruritis such as low humidity or dry skin, skin diseases such as scabies, insect bites; systemic causes such as infectious causes.

Some kinds of itching are relieved by antihistamine but many others are not. Therefore, there is a need for improved treatments to relieve severe itching. The present invention provides a composition and method for treating Pruritis independent of systemic effects on the central nervous system.

SUMMARY OF THE INVENTION

The present invention provides an improved composition and method of treating severe itching comprising topically administering a therapeutically effective amount of colloidal sulfur suspended in a pharmaceutically acceptable carrier including a vicinal diketone and aliphatic poly-alcohol which may be esterified by a fatty acid.

DETAILED DESCRIPTION OF THE PREFERRED EMBODIMENTS

It has now been discovered that elemental sulfur, dispersed in a diketone with a poly-alcohol is effective for palliative treatment of Pruritis, regardless of the etiology of the itching. Or particularly, elemental sulfur, which may be in the form of flowers of sulfur or finely divided sulfur in relatively pure form from commercially available sources, may be dispersed in a vicinal diketone, to form a colloidal solution which may then be dispersed in an aqueous, fat or oil carrier fluid in which sulfur is otherwise insoluble, to form a stable dispersion of colloidal sulfur in a concentrate of 1 to 7 weight percent sulfur which advantageously may be used alone or in a combination with other antipruritic compounds to treat Pruritis.

More particularly, in accordance with the preferred embodiment of my invention, a dispersion of colloidal sulfur is formed by beating sulfur in a polyalcohol or ether or ester derivative thereof in a mixture with a diketone to produce a colloidal sulfur solution which may then be mixed in a carrier fluid, e.g. aqueous media, fats such as cream commonly employed in producing salves and ointments, or mineral or vegetable oils commonly used in producing dermatological formulations, and applied topically. Examples of useful products include creams, lotions, solutions, ointments and unguents containing colloidal sulfur solutions.

The concentration of diketone in the formulation is not critical and can vary over a wide range. Typically, however, the diketone will be present in an amount in a range of 5–40% by weight which is sufficient to permit about 7% by weight dispersion of sulfur in the formulation.

The formulation may contain additional ingredients on an optional basis, including both those which are biologically active and those which are biologically inactive. Examples of biologically active ingredients are amine-and- "caine"- type local anesthetics, antihistamines, corticosteroids, alcohol's, counterirritants and combinations of these agents. Specific examples within these groups include butaman, benzocaine, dibucaine, paramoxine, dimethisoquin, dyclonine, lidocaine, tetracaine, camphor, benzyl alcohol, menthyl, phenol, phenolated sodium, resorcinol, tar, camphorated metacresol, diphenhydramine, tripelennamine, hydrocortisone, histamine, methyl nicotinate, capsicum, methyl salicylate, turpentine oil, allyl isothiocyanate, ammonia, and salicylic acid. The concentrations of these active ingredients can range from 0.025% to 60%, the most appropriate amounts in each case depending on the agents. Appropriate concentration ranges from any particular agent will be apparent to those skilled in the Art.

The diketone should be one of several small molecular weight diketones so as to preserve its water solubility. Preferred are lower molecular weight ketones and diketones such as hydroxy diketone, diacetyl, or homologs thereof.

The invention will now be further described in connection with the following examples:

EXAMPLE I

Seventy five (75) g. of glycerol monostearate is heated to 130 degrees C. and 10 g. of diacetyl are added plus 8 g. of powdered elemental sulfur are added. The mix is stirred and the decanted liquid is poured into 100 ml. of water. The mixture is a milky colloidal solution suitable for topical application.

EXAMPLE II

Fifty (50) g. of propylene glycol is heated to 110 degrees C. with 10 g. of diacetyl. Then 5 g. of powdered elemental sulfur is added and kept at 110 degrees C. Then the solution is poured into 1% acacia solution to form a stable colloidal solution for topical application.

The preparation formed in Examples I and II were swabbed on itchy skin of volunteers who reported almost instant secession of itching.

While only preferred embodiments of the invention have been described, various changes may be made without departing from the spirit and scope of the invention.

I claim:

1. A composition of matter comprising a therapeutically effective amount of a colloidal suspension of sulfur in a diketone selected from the group consisting of hydroxy diketone, methyl ethyl diketone, dimethyldiketone and diethyldiketone.

2. The composition according to claim 1, administered in a carrier to form a cream, lotion, solution, ointment or urguent for typical application.

3. The composition according to claim 2, further comprising a local anesthetic, an antihistamine, a corticosteroid, an alcohol or a counterirritant.

4. The composition of claim 1, wherein the colloidal sulfur comprises 1–7 wt % of the composition.

5. The composition of claim 1, wherein said diketone comprises 5–40 wt % of the composition.

6. The composition of claim 1, further comprising a carrier comprising glycerol monostearate.

7. The composition of claim 1, further comprising a carrier comprising propylene glycol.

8. A method of relieving severe itching in patients in need of such treatment, which method comprises topically administering a composition comprising a colloidal suspension of sulfur in a diketone selected from the group consisting of hydroxy diketone, methyl ethyl diketone, dimethyldiketone, and diethyldiketone to the patient in need of such treatment.

9. The method according to claim 8, wherein the composition is administered in a carrier which forms a cream, lotion, solution, ointment or urguent.

10. The method according to claim 8, wherein the composition further comprises a local anesthetic, an antihistamine, a corticosteroid, alcohol or a counterirritant.

11. The method according to claim 8, wherein the colloidal sulfur comprises 1–7 wt % of the composition.

12. The method according to claim 8, wherein said diketone comprises 5–40 wt % of the composition.

13. The method according to claim 8, wherein the composition is administered in a carrier comprising glycerol monostearate.

14. The method according to claim 8, wherein the composition is administered in a carrier comprising propylene glycol.

* * * * *